US008435224B2

(12) United States Patent
Claussen et al.

(10) Patent No.: US 8,435,224 B2
(45) Date of Patent: May 7, 2013

(54) MATERIALS FOR FACILITATING ADMINISTRATION OF DIMETHYL SULFOXIDE (DMSO) AND RELATED COMPOUNDS

(75) Inventors: Harvey L. Claussen, Portland, OR (US); Colette Cozean, Lake Forest, CA (US); Jack De La Torre, Gig Harbor, WA (US)

(73) Assignee: Abela Pharmaceuticals, Inc., Lake Forest, CA (US)

( * ) Notice: Subject to any disclaimer, the term of this patent is extended or adjusted under 35 U.S.C. 154(b) by 587 days.

(21) Appl. No.: 12/066,480

(22) PCT Filed: Sep. 11, 2006

(86) PCT No.: PCT/US2006/035499

§ 371 (c)(1), (2), (4) Date: Mar. 11, 2008

(87) PCT Pub. No.: WO2007/033180

PCT Pub. Date: Mar. 22, 2007

(65) Prior Publication Data

US 2008/0228161 A1 Sep. 18, 2008

Related U.S. Application Data

(60) Provisional application No. 60/716,265, filed on Sep. 12, 2005, provisional application No. 60/716,368, filed on Sep. 12, 2005.

(51) Int. Cl.

| | |
|---|---|
| ***A61M 39/00*** | (2006.01) |
| *A61M 39/08* | (2006.01) |
| *A61B 19/00* | (2006.01) |

(52) U.S. Cl.

USPC .......... 604/404; 604/403; 604/408; 604/6.15; 604/317; 604/319

(58) Field of Classification Search .................... 604/48, 604/93.01, 404, 408, 410, 416; 206/828; 220/500; 383/38, 109; 428/34.1; 137/15.11; 436/3

See application file for complete search history.

(56) References Cited

U.S. PATENT DOCUMENTS

| | | | |
|---|---|---|---|
| 3,334,012 A | | 8/1967 | Herschler |
| 3,361,555 A | | 1/1968 | Herschler |
| 3,393,080 A | | 7/1968 | Erdi et al. |
| 3,419,619 A | | 12/1968 | Soder et al. |
| 3,482,572 A | | 12/1969 | Grosclaude et al. |
| 3,527,863 A | | 9/1970 | Weichselbaum |
| 3,549,770 A | | 12/1970 | Herschler et al. |
| 3,549,771 A | | 12/1970 | Herschler |
| 3,551,554 A | | 12/1970 | Herschler |
| 3,558,434 A | | 1/1971 | Herschler |
| 3,573,214 A | | 3/1971 | Kollonitsch |
| 3,592,936 A | | 7/1971 | Marcus et al. |
| 3,654,165 A | | 4/1972 | Bryant et al. |
| 3,675,654 A | * | 7/1972 | Baker et al. .................. 604/361 |
| 3,690,808 A | | 9/1972 | St. Pierre |
| 3,711,606 A | | 1/1973 | Herschler |
| 3,740,420 A | | 6/1973 | Herschler et al. |
| 3,773,838 A | | 11/1973 | Andruski et al. |
| 3,790,682 A | | 2/1974 | Herschler et al. |
| 3,823,676 A | | 7/1974 | Cook et al. |
| 3,852,408 A | | 12/1974 | Ewan et al. |
| 3,861,894 A | | 1/1975 | Marsh |
| 3,881,003 A | | 4/1975 | Rehm |
| 3,948,617 A | | 4/1976 | Withorn |
| 3,972,962 A | | 8/1976 | Williams et al. |
| 3,976,747 A | | 8/1976 | Shale et al. |
| 3,988,129 A | | 10/1976 | Fornoff et al. |
| 3,996,295 A | | 12/1976 | Goeb |
| 4,015,025 A | | 3/1977 | Szczesniak |
| 4,112,946 A | | 9/1978 | Herschler |
| 4,125,589 A | | 11/1978 | deVries |
| 4,129,122 A | | 12/1978 | Dout et al. |
| 4,169,550 A | | 10/1979 | Williams |
| 4,177,267 A | | 12/1979 | Herschler |
| 4,194,628 A | | 3/1980 | Campos |
| 4,202,676 A | | 5/1980 | Pelosi, Jr. et al. |
| 4,212,392 A | | 7/1980 | McKenzie |
| 4,225,381 A | | 9/1980 | Ishikawa et al. |
| 4,252,054 A | | 2/1981 | Bakels |

(Continued)

FOREIGN PATENT DOCUMENTS

| | | |
|---|---|---|
| CA | 2617934 | 2/2007 |
| EP | 0827744 | 3/1998 |

(Continued)

OTHER PUBLICATIONS

"Guidance on Medical Device Patient Labeling" accessed Mar. 10, 2010. http://www.fda.gov/MedicalDevices/DeviceRegulationandGuidance/GuidanceDocuments/ucm070782.htm.*

(Continued)

*Primary Examiner* — Leslie R. Deak
*Assistant Examiner* — Adam Marcetich
(74) *Attorney, Agent, or Firm* — Knobbe Martens Olson & Bear, LLP

(57) ABSTRACT

The invention relates generally to materials for facilitating the administration of dimethyl sulfoxide (DMSO) and related compounds. In one embodiment, the invention comprises a kit comprising items used for the safe and effective administration of DMSO. In another embodiment, the invention relates to indicating containers for holding or delivering DMSO.

13 Claims, No Drawings

U.S. PATENT DOCUMENTS 4,256,728 A 3/1981 Nishino et al.
4,277,450 A 7/1981 Dilworth
4,296,104 A 10/1981 Herschler
4,296,130 A 10/1981 Herschler
4,307,067 A 12/1981 Tagawa et al.
4,309,393 A 1/1982 Nguyen
4,316,795 A 2/1982 Mooi
4,333,922 A 6/1982 Herschler
4,335,148 A 6/1982 Vidal et al.
4,341,675 A 7/1982 Nakamura
4,350,245 A 9/1982 Elstner
4,357,288 A 11/1982 Oas et al.
4,369,190 A 1/1983 Schulte
4,372,915 A 2/1983 Neti et al.
4,413,109 A 11/1983 Haas
4,424,330 A 1/1984 Raviola
4,469,702 A 9/1984 Schulte
4,477,469 A 10/1984 Herschler
4,491,563 A 1/1985 Reusser et al.
4,493,930 A 1/1985 Klayman et al.
4,497,824 A 2/1985 Schulte
4,505,708 A 3/1985 Gajewski et al.
4,507,114 A * 3/1985 Bohman et al. ............... 604/111
4,510,292 A 4/1985 Chiba et al.
4,512,245 A 4/1985 Goldman
4,514,421 A 4/1985 Herschler
4,545,414 A 10/1985 Baum
4,550,010 A 10/1985 Chelu
4,559,329 A 12/1985 Herschler
4,568,547 A 2/1986 Herschler
4,575,515 A 3/1986 Sandborn
4,591,497 A 5/1986 Naito et al.
4,595,102 A 6/1986 Cianci et al.
4,600,002 A 7/1986 Maryyanek et al.
4,616,039 A 10/1986 Herschler
4,616,064 A 10/1986 Zukosky et al.
4,622,221 A 11/1986 Schleppnik
4,626,530 A 12/1986 Schulte
4,634,588 A 1/1987 Moroe
4,642,177 A 2/1987 Mester et al.
4,652,557 A 3/1987 Sandborn
4,655,148 A 4/1987 Winship
4,656,094 A 4/1987 Kojima et al.
4,686,204 A 8/1987 Mester et al.
4,710,353 A * 12/1987 Tanaka et al. .............. 422/82.11
4,719,105 A 1/1988 Schleppnik
4,721,813 A 1/1988 Mark et al.
4,725,290 A 2/1988 Ohlmeyer et al.
4,728,712 A 3/1988 Singh et al.
4,729,835 A 3/1988 McNeillie et al.
4,737,173 A 4/1988 Kudirka et al.
4,747,845 A 5/1988 Korol
4,751,241 A 6/1988 Motoyama et al.
4,778,697 A 10/1988 Genske et al.
4,784,909 A 11/1988 Emi et al.
4,796,790 A 1/1989 Hamilton
4,797,274 A 1/1989 Miki et al.
4,803,047 A 2/1989 Pluim, Jr.
4,830,718 A 5/1989 Stauffer
4,834,721 A 5/1989 Onohara et al.
4,850,268 A 7/1989 Saito et al.
4,863,687 A 9/1989 Stevens et al.
4,863,748 A 9/1989 Herschler
4,887,751 A 12/1989 Lehman
4,902,489 A 2/1990 Watanabe
4,902,558 A 2/1990 Henriksen
4,904,520 A 2/1990 Dumas et al.
4,910,803 A * 3/1990 Cukier ............................. 2/168
4,911,691 A 3/1990 Aniuk et al.
4,914,135 A 4/1990 Herschler
4,916,767 A 4/1990 Uetake et al.
4,919,925 A 4/1990 Ueda et al.
4,931,276 A 6/1990 Franco et al.
4,937,115 A 6/1990 Leatherman
4,940,405 A 7/1990 Kelly
4,940,658 A 7/1990 Allen et al.
4,941,991 A 7/1990 Rajamannan
4,946,720 A 8/1990 Oishi et al.
4,948,643 A 8/1990 Mueller
4,948,787 A 8/1990 Chen et al.
4,956,183 A 9/1990 Miki et al.
4,973,605 A 11/1990 Herschler
4,978,687 A 12/1990 Pascuchi
4,980,045 A 12/1990 Krishna et al.
4,988,505 A 1/1991 Watanabe et al.
4,990,311 A 2/1991 Hirai et al.
4,994,245 A 2/1991 Murray et al.
5,001,794 A 3/1991 Uetake et al.
5,006,510 A 4/1991 Ellis
5,007,999 A 4/1991 Chin
5,032,613 A 7/1991 Watson
5,041,273 A 8/1991 Rock
5,049,159 A 9/1991 Yamaji et al.
5,049,163 A 9/1991 Huang et al.
5,055,279 A 10/1991 Hirt et al.
5,059,477 A * 10/1991 Henriksen ..................... 428/220
5,070,597 A 12/1991 Holt et al.
5,071,622 A 12/1991 Dunson, Jr.
5,071,686 A 12/1991 Genske et al.
5,071,878 A 12/1991 Herschler
5,083,558 A 1/1992 Thomas et al.
5,086,804 A 2/1992 Ngai
5,087,673 A 2/1992 Watanabe et al.
5,091,180 A 2/1992 Walker et al.
5,117,821 A 6/1992 White
5,133,788 A 7/1992 Backus
5,135,904 A 8/1992 Kamiya et al.
5,139,831 A 8/1992 Mueller
5,143,831 A 9/1992 Wong et al.
5,145,657 A 9/1992 Kobayashi et al.
5,149,576 A 9/1992 Potts et al.
5,152,814 A 10/1992 Nelson
5,160,707 A 11/1992 Murray et al.
5,169,217 A 12/1992 Orchard et al.
5,183,656 A 2/1993 Uesaka et al.
5,190,640 A 3/1993 Roof et al.
5,192,272 A * 3/1993 Faure ............................ 604/141
5,192,342 A 3/1993 Baron et al.
5,192,498 A 3/1993 Chen et al.
5,199,263 A 4/1993 Green et al.
5,207,303 A 5/1993 Oswalt et al.
5,213,680 A 5/1993 Kremer et al.
5,218,036 A 6/1993 Kagawa et al.
5,218,147 A 6/1993 Shaw
5,240,478 A 8/1993 Messina
5,260,090 A 11/1993 Isao
5,269,294 A 12/1993 Rogozinski
5,290,331 A 3/1994 Miles et al.
5,335,373 A * 8/1994 Dresdner et al. ............... 2/161.7
5,336,431 A 8/1994 Richards et al.
5,344,529 A 9/1994 Stauffer
5,356,709 A 10/1994 Woo et al.
5,358,443 A 10/1994 Mitchell et al.
5,409,769 A 4/1995 Fukumoto et al.
5,415,180 A 5/1995 Horan
5,419,812 A 5/1995 Beal
5,439,454 A 8/1995 Lo et al.
5,441,729 A 8/1995 Salce et al.
5,458,848 A 10/1995 Burgaud
5,458,861 A 10/1995 Buchanan et al.
5,460,625 A * 10/1995 Johnson ........................ 604/403
5,466,757 A 11/1995 Watanabe et al.
5,480,860 A 1/1996 Dillon
5,486,387 A 1/1996 Mueller
5,487,766 A 1/1996 Vannier
5,494,587 A 2/1996 Morlec et al.
5,512,144 A 4/1996 Stauffer
5,516,526 A 5/1996 De la Torre
5,521,268 A 5/1996 Ghyzel et al.
5,531,987 A 7/1996 Bauer et al.
5,538,545 A 7/1996 Dauber et al.
5,562,127 A 10/1996 Fanselow et al.
5,569,679 A 10/1996 Jacob
5,578,540 A 11/1996 Banzi et al.
5,584,986 A 12/1996 Bartholic
5,603,696 A 2/1997 Williams et al.
5,605,635 A 2/1997 David 5,616,408 A 4/1997 Oleszczuk et al.
5,620,760 A 4/1997 Galimberti et al.
5,624,649 A 4/1997 Gal
5,650,329 A * 7/1997 Warner ........................ 436/101
5,654,061 A 8/1997 Visioli
5,658,801 A 8/1997 Poissant et al.
5,667,799 A 9/1997 Caldwell et al.
5,703,152 A 12/1997 Ohama
5,712,044 A 1/1998 Fanselow et al.
5,725,893 A 3/1998 Pittet et al.
5,753,696 A 5/1998 Shealy et al.
5,761,362 A 6/1998 Yang et al.
5,779,679 A 7/1998 Shaw
5,783,269 A 7/1998 Heilmann et al.
5,789,046 A 8/1998 Mueller
5,792,505 A 8/1998 Fulger et al.
5,803,130 A 9/1998 Robben et al.
5,803,249 A 9/1998 Harsanyi, Jr. et al.
5,843,420 A 12/1998 Bauer et al.
5,849,846 A 12/1998 Chen et al.
5,861,096 A 1/1999 Mason et al.
5,871,562 A 2/1999 Culoso
5,885,566 A 3/1999 Goldberg
5,891,508 A 4/1999 Barnum
5,919,877 A 7/1999 Tanaglia
5,928,744 A 7/1999 Heilmann et al.
5,931,303 A 8/1999 Salvadori
5,935,412 A 8/1999 Brainard, II
5,935,547 A 8/1999 LeComte et al.
5,948,398 A 9/1999 Hanamoto et al.
5,958,502 A 9/1999 Fulger et al.
5,965,276 A * 10/1999 Shlenker et al. .............. 428/492
5,967,061 A 10/1999 Ashworth et al.
5,972,993 A 10/1999 Ptchelintsev
5,989,497 A 11/1999 Labonte, Jr.
5,998,019 A 12/1999 Rosenbaum et al.
6,007,520 A 12/1999 Sudo
6,010,666 A 1/2000 Kurokawa et al.
6,012,586 A 1/2000 Misra
6,015,536 A 1/2000 Lokkesmoe et al.
6,030,494 A 2/2000 Hupa et al.
6,042,640 A 3/2000 Isganitis et al.
6,045,596 A 4/2000 Holland, Jr. et al.
6,048,733 A 4/2000 Machino et al.
6,057,018 A 5/2000 Schmidt
6,060,083 A 5/2000 Dorr et al.
6,060,152 A * 5/2000 Murchie .................... 428/313.5
D427,299 S 6/2000 Haslebacher
6,070,578 A 6/2000 Baughman et al.
6,077,335 A 6/2000 Schneider et al.
6,090,076 A 7/2000 Lane, Jr.
6,094,549 A 7/2000 Hiraoka et al.
6,099,607 A 8/2000 Haslebacher
6,106,502 A 8/2000 Richmond
6,106,596 A 8/2000 Haramoto et al.
6,110,176 A 8/2000 Shapira
6,114,586 A 9/2000 Devaux et al.
D431,353 S 10/2000 Mellin
D431,902 S 10/2000 Mellin
6,183,708 B1 2/2001 Hei et al.
6,183,758 B1 2/2001 Scott
6,197,288 B1 3/2001 Mankoo
6,207,106 B1 3/2001 Kurokawa et al.
6,221,325 B1 4/2001 Brown et al.
6,228,960 B1 5/2001 Tanaglia
6,238,767 B1 5/2001 McCormack et al.
6,248,733 B1 6/2001 Landgrebe et al.
6,261,655 B1 7/2001 Rosenbaum et al.
6,267,941 B1 7/2001 Sata
6,277,344 B1 8/2001 Hei et al.
6,294,161 B1 9/2001 Hiramoto et al.
6,303,200 B1 10/2001 Woo et al.
6,312,713 B1 11/2001 Korol et al.
6,318,075 B1 11/2001 Gunther et al.
6,348,177 B1 2/2002 Bartley et al.
6,349,826 B1 2/2002 Kapik et al.
6,365,099 B1 4/2002 Castrantas et al.
6,403,642 B1 6/2002 Berg
6,403,739 B1 6/2002 Tanaglia et al.
6,406,767 B1 6/2002 Mueller
6,412,639 B1 7/2002 Hickey
6,414,194 B1 7/2002 Bloom, Jr. et al.
6,416,772 B1 7/2002 Van Engelen et al.
6,418,932 B2 7/2002 Paschal, Jr. et al.
6,426,112 B1 7/2002 Boatright
6,426,370 B1 7/2002 Hofschneider
6,432,891 B1 8/2002 O'Connor
6,440,391 B1 8/2002 Jacob
6,454,097 B1 9/2002 Blanco
6,458,828 B1 10/2002 Sakurai et al.
6,460,702 B2 10/2002 Hammond
6,461,631 B1 10/2002 Dunn et al.
6,465,068 B1 10/2002 Patel et al.
6,468,259 B1 * 10/2002 Loretti et al. ................ 604/410
6,475,466 B1 11/2002 Ricci et al.
6,479,150 B1 11/2002 Liu et al.
6,479,488 B1 11/2002 Di-Fabio et al.
6,482,377 B2 11/2002 Bartley et al.
6,495,096 B1 12/2002 Hamaguchi et al.
6,528,080 B2 3/2003 Dunn et al.
6,531,111 B1 3/2003 Whalen, II et al.
6,552,231 B2 4/2003 Jones et al.
6,562,447 B2 5/2003 Wu et al.
6,579,444 B2 6/2003 Feimer et al.
6,579,543 B1 6/2003 McClung
6,599,472 B1 7/2003 Hudson
6,620,911 B1 9/2003 Pettit et al.
6,638,605 B1 10/2003 Ankuda, Jr. et al.
6,639,110 B2 10/2003 Fremy
6,649,193 B1 11/2003 Colic
6,652,845 B2 11/2003 Hu et al.
6,653,352 B2 11/2003 Barr et al.
6,656,723 B1 12/2003 Phillips
6,663,679 B1 * 12/2003 Duncan ..................... 73/335.01
6,680,194 B1 1/2004 Turner
6,706,257 B1 3/2004 McCook et al.
6,718,914 B2 4/2004 Riddles
6,722,295 B2 4/2004 Zauderer
6,723,349 B1 4/2004 Hill et al.
6,723,399 B2 4/2004 Chundury et al.
6,734,263 B2 5/2004 Eadara et al.
6,737,031 B2 5/2004 Beal et al.
6,737,089 B2 5/2004 Wadsworth et al.
6,743,523 B1 6/2004 Woo et al.
6,743,951 B2 6/2004 Fremy
6,761,169 B2 7/2004 Eswarappa
6,761,912 B2 7/2004 Forusz et al.
6,764,566 B1 7/2004 Griesbach, III et al.
6,783,004 B1 8/2004 Rinner
RE38,597 E 9/2004 Lane, Jr.
6,796,958 B2 9/2004 Chen et al.
6,822,015 B2 11/2004 Muraki
6,830,794 B2 12/2004 Cartledge et al.
6,844,430 B2 1/2005 Pesce et al.
6,846,535 B2 1/2005 De Groot et al.
6,858,192 B2 2/2005 Graham et al.
6,872,241 B2 3/2005 Soane et al.
6,881,419 B2 4/2005 Lovett
6,884,797 B2 4/2005 Hofmann
6,890,373 B2 5/2005 Nemoto et al.
6,902,714 B2 6/2005 Skaarup Jensen et al.
6,908,885 B2 6/2005 Bengs et al.
6,927,305 B2 8/2005 Choudary et al.
7,057,016 B2 6/2006 Cerletti
7,203,974 B2 * 4/2007 Jones et al. ....................... 2/456
7,282,224 B1 10/2007 Roederer et al.
7,371,407 B2 5/2008 Farmer
7,381,521 B2 6/2008 Whitaker et al.
7,955,418 B2 6/2011 Claussen et al.
8,298,320 B2 10/2012 Cozean
2001/0005766 A1 6/2001 Fremy
2001/0018095 A1 * 8/2001 Shlenker et al. .............. 427/337
2001/0047038 A1 11/2001 Moorman et al.
2002/0015762 A1 2/2002 Quinlan
2002/0025983 A1 2/2002 Horrobin
2002/0032131 A1 3/2002 O'Connor
2002/0043501 A1 4/2002 Irvine
2002/0090398 A1 7/2002 Dunn et al.

2002/0110549 A1 8/2002 Till
2002/0115729 A1 8/2002 Yang
2002/0131933 A1 9/2002 Delmotte
2002/0133100 A1 9/2002 Paschal, Jr. et al.
2002/0151753 A1 10/2002 Fremy
2002/0156326 A1 10/2002 Fremy
2002/0182263 A1 12/2002 Stenti et al.
2003/0017183 A1 1/2003 Pollock
2003/0032616 A1 2/2003 Moskowitz et al.
2003/0082321 A1* 5/2003 Kennedy et al. ............ 428/35.7
2003/0085170 A1 5/2003 Scranton et al.
2003/0108810 A1 6/2003 Williamson et al.
2003/0118672 A1 6/2003 McPeak et al.
2003/0133959 A1 7/2003 Shacknai et al.
2003/0152862 A1 8/2003 Williamson et al.
2003/0157006 A1 8/2003 Hei et al.
2003/0167033 A1* 9/2003 Chen et al. ..................... 604/20
2003/0190266 A1 10/2003 Tsurumi
2003/0203009 A1 10/2003 MacDonald
2003/0203484 A1 10/2003 Black et al.
2004/0016410 A1 1/2004 Riddles
2004/0039066 A1 2/2004 Crea
2004/0048376 A1 3/2004 Chabot et al.
2004/0057972 A2 3/2004 Shacknai et al.
2004/0074212 A1 4/2004 Yachi et al.
2004/0081673 A1 4/2004 Rayner et al.
2004/0082667 A1 4/2004 McCadden et al.
2004/0086888 A1 5/2004 Kornblith et al.
2004/0087669 A1 5/2004 Hausmanns et al.
2004/0105943 A1* 6/2004 Hoerner et al. ............. 428/35.7
2004/0115818 A1* 6/2004 Puri et al. ......................... 436/3
2004/0131806 A1* 7/2004 Barmore et al. ............ 428/34.2
2004/0137136 A1 7/2004 Zheng et al.
2004/0151826 A1 8/2004 Milligan
2004/0154220 A1 8/2004 Holcomb
2004/0156742 A1 8/2004 Milan et al.
2004/0157802 A1 8/2004 Horwitz et al.
2004/0186316 A1 9/2004 Choudary et al.
2004/0197339 A1 10/2004 Brown
2004/0213755 A1 10/2004 Hochwalt et al.
2004/0213774 A9 10/2004 Till
2004/0219126 A1 11/2004 Seto et al.
2004/0242818 A1 12/2004 Williamson et al.
2004/0265291 A1 12/2004 Drake et al.
2005/0025840 A1 2/2005 Revnolds
2005/0031651 A1 2/2005 Gervais et al.
2005/0031761 A1 2/2005 Brucker et al.
2005/0035062 A1 2/2005 Hiltzik et al.
2005/0054875 A1 3/2005 Hei et al.
2005/0058630 A1 3/2005 Harris et al.
2005/0069598 A1 3/2005 Ribnicky et al.
2005/0084412 A1 4/2005 MacDonald et al.
2005/0084438 A1 4/2005 Do et al.
2005/0084464 A1 4/2005 McGrath et al.
2005/0084474 A1 4/2005 Wu et al.
2005/0092070 A1* 5/2005 Bhatti .............................. 73/40
2005/0092761 A1* 5/2005 Marganski et al. .......... 220/724
2005/0095653 A1 5/2005 Goldstein et al.
2005/0112085 A1 5/2005 MacDonald et al.
2005/0112176 A1 5/2005 Dopson et al.
2005/0112177 A1 5/2005 Dopson et al.
2005/0115895 A1 6/2005 Simpson et al.
2005/0136082 A1 6/2005 Soane et al.
2005/0136125 A1 6/2005 Roth
2005/0142096 A1 6/2005 Wegner
2005/0147692 A1 7/2005 Roth
2005/0158406 A1 7/2005 McPeak et al.
2005/0158424 A1 7/2005 Nakano et al.
2005/0169826 A1 8/2005 Li
2005/0176778 A1 8/2005 Vermeer
2005/0181048 A1 8/2005 Romero
2005/0182076 A1 8/2005 Pacheco et al.
2005/0187124 A1 8/2005 Li et al.
2005/0191343 A1 9/2005 Liang
2005/0215515 A1 9/2005 Bucolo et al.
2005/0222275 A1 10/2005 Gabizon et al.
2005/0224409 A1 10/2005 Harshman et al.
2005/0226827 A1 10/2005 Ho
2005/0227910 A1 10/2005 Yang et al.
2005/0260306 A1 11/2005 Baldus
2005/0261257 A1 11/2005 Vermeer
2005/0265979 A1 12/2005 Aoki et al.
2005/0266064 A1 12/2005 McCarthy
2005/0281883 A1 12/2005 Daniloff et al.
2006/0003069 A1 1/2006 Zheng et al.
2006/0006120 A1 1/2006 Chen et al.
2006/0006121 A1 1/2006 Simpson et al.
2006/0018933 A1 1/2006 Vaya et al.
2006/0018934 A1 1/2006 Vaya et al.
2006/0024365 A1 2/2006 Vaya et al.
2006/0052438 A1 3/2006 Ho et al.
2006/0127508 A1 6/2006 Larkins
2006/0143767 A1* 7/2006 Yang et al. ......................... 2/16
2006/0166948 A1 7/2006 Vermeer
2006/0177398 A1 8/2006 McCook et al.
2006/0194759 A1 8/2006 Eidelson
2006/0210646 A1 9/2006 Oku et al.
2006/0281822 A1 12/2006 Appleton
2007/0025950 A1 2/2007 Elson
2007/0028772 A1 2/2007 Jain et al.
2007/0048386 A1 3/2007 Mallozzi, Sr. et al.
2007/0180544 A1 8/2007 Taylor et al.
2007/0183936 A1 8/2007 Newsam et al.
2007/0243146 A1 10/2007 Klock
2007/0264212 A1 11/2007 Ho
2007/0270358 A1 11/2007 Paoliambrosi
2007/0292493 A1 12/2007 Brierre
2008/0038219 A1 2/2008 Mosbaugh et al.
2008/0076831 A1 3/2008 Goetz
2008/0102107 A1 5/2008 Lewellyn et al.
2008/0146458 A1 6/2008 Hollingsworth et al.
2008/0193427 A1 8/2008 Kaesler et al.
2008/0228161 A1 9/2008 Claussen et al.
2008/0249082 A1 10/2008 Hollander
2008/0251081 A1 10/2008 Claussen et al.
2008/0260871 A1 10/2008 Fruitman
2008/0274153 A1 11/2008 Farmer
2008/0275015 A1 11/2008 Potter
2008/0300311 A1 12/2008 Kisak et al.
2008/0317680 A1 12/2008 Dueva-Koganov et al.
2008/0319092 A1 12/2008 Singh et al.
2009/0215888 A1 8/2009 Jagat et al.
2009/0312273 A1 12/2009 De La Torre
2009/0324784 A1 12/2009 McLellan et al.
2011/0105623 A1 5/2011 Benjamin et al.
2011/0136210 A1 6/2011 Benjamin et al.
2011/0203583 A1 8/2011 Cozean et al.
2011/0203585 A1 8/2011 Cozean et al.

FOREIGN PATENT DOCUMENTS

EP 0976726 2/2000
GB 2 028 162 12/1979
JP 2005330199 12/2005
WO WO 85/00108 1/1985
WO WO 94/05272 3/1994
WO WO 95/03753 2/1995
WO WO 00/64868 11/2000
WO WO 01/73096 10/2001
WO WO 03/015760 2/2003
WO WO 03/101415 12/2003
WO WO 2004/064877 8/2004
WO WO 2004/067013 8/2004
WO WO 2004/093541 11/2004
WO WO 2004/100896 11/2004
WO WO 2005/054553 6/2005
WO WO 2005/115546 12/2005
WO WO 2005/117913 12/2005
WO WO 2006/129149 12/2006
WO WO 2006/135854 12/2006
WO WO 2007/009245 1/2007
WO WO 2007/016766 2/2007
WO WO 2007/033082 3/2007
WO WO 2007/033083 3/2007
WO WO 2007/056205 5/2007
WO WO 2007/098591 9/2007
WO WO 2007/126191 11/2007
WO WO 2008/049020 4/2008
WO WO 2008/098871 8/2008

| | | |
|---|---|---|
| WO | WO 2010/054093 | 5/2010 |
| WO | WO 2010/062721 | 6/2010 |
| WO | WO 2011/053848 | 5/2011 |
| WO | WO 2011/053854 | 5/2011 |
| WO | WO 2011/053874 | 5/2011 |
| WO | WO 2011/053875 | 5/2011 |
| WO | WO 2011/123695 | 10/2011 |

OTHER PUBLICATIONS

Online encyclopedia article on "Scrubs," accessed Mar. 10, 2010. http://en.wikipedia.org/wiki/Scrubs_(clothing).*

Aleksevich Ial, Piletskaia IG, Nikonorova VP. *Increase in the sensitivity of the microflora of pathological gingival pockets to streptomycin under the influence of dimexide and trypsin*. Mikrobiol Zh. Nov.-Dec. 1973; 35(6):766-9.

Berry et al. *Natural Gas Odorants Desulfurization*, (2004) AlChE Annual National Meeting, Austin, Texas, Nov. 7-12.

Blumenthal L, Fuchs M. *The Clinical Use of Dimethyl Sulfoxide on Various Headaches, Musculoskeletal and Other General Medical Disorders*. Annals New York Academy of Sciences 1967:572-585.

Bookman A, Williams S, Shainhouse J. *Effect of a topical diclofenac solution for relieving symptoms of primary osteoarthritis of the knee: a randomized controlled trial*. CMAJ Aug. 17, 2004; 171(4):333-338.

Brayton CF. *Dimethyl Sulfoxide (DMSO); A Review*. The Cornel Veterinarian. Jan. 1986; 76(1):61-90.

Brechner V, Cohen D, Pretsky I. *Dermal Anesthesia by the Topical Application of Tetracaine Base Dissolved in Dimethyl Sulfoxide*, Annals New York Academy of Sciences. 1967:524-531.

Brien et al. *Systematic review of the nutritional supplements dimethyl sulfoxide (DMSO) and methylsulfonylmethane (MSM) in the treatment of osteoarthritis*. Osteoarthritis and Cartilage (2008) 16:1277-1288.

Brien S, Prescott P, Lewith G. *Meta-analysis of the Related Nutritional Supplements Dimethyl Sulfoxide and Methylsulfonlymethane in the Treatment of Osteoarthritis of the Knee*. eCAM Advance Access published May 27, 2009 in 10 pages.

Brown JH. *Clinical Experience with DMSO in Acute Musculoskeletal Conditions, Comparing a Noncontrolled Series with a Controlled Double Blind Study*. Ann NY Acad Sci 1967; 141(1):496-505.

Debi R, et al. *The Role of MSM in Knee Osteoarthritis: A Double Blind, RandomizedProspective Study*. Osteoarthritis and Cartilage (2008) 15 Supplemental C:C231 (426).

Demos C et al. *Dimethyl Sulfoxide in Musculoskeletal Disorders*. Ann NY Acad Sci 1967:517-523.

Eberhardt et al. *DMSO in patients with Active Gonarthrosis. A double-blind, placebo-controlled Phase III Study*. Fortschr Med, Nov. 10, 1995: 113(31):446-450.

Evans MS, Reid KH, Sharp JB. *Dimethylsulfoxide (DMSO) blocks conduction in peripheral nerve C fibers: a possible mechanism of analgesia*. Neuroscience Letters, 150 (1993):145-148.

Feldman WE, Punch JD, Holden PC. *In vivo and in vitro effects of dimethyl sulfoxide on streptomycin-sensitive and -resistant Escherichia coli*. Ann NY Acad Sci, Jan. 27, 1975; 243:269-77.

Florain, The Solid State Structures of the Dimethylformamide and Dimethylsulfoxide Complexes of Dioxodichloromolybdenum (VI), ProQuest, 30-07B (1969), pp. 66.

Glasser D. *Dimethylsulfoxide (DMSO) "resensibilization" as potential chemotherapy for opportunistic mycobacterial disease*. Am Rev Respir Dis. Nov. 1978; 118(5):969-70.

Gorbach IN, *Samtsov vs. Therapeutic possibilities of inhalation of rifampicin with dimexide in phthisiopulmonology*. Probl Tuberk. 1991; (3):34-6.

Haigler HJ et al. *Comparison of the Analgesic Effects of Dimethyl Sulfoxide and Morphine*, Ann NY Acad Sci 1983; (411):19-27.

Hasegawa T, *Suppressive Effects of Methylsulfonylmethane (MSM) on Type II Collagen-induced Arthritis in DBA/1J Mice*. Jpn Pharmacol Ther 2004; 32 (7):421-427.

Jacob S, Appleton J. *MSM: The Definitive Guide*—Chapter 6, 45-54, Part II, Chapter 7, 57-68, Chapter 8, 69-76, Chapter 10, 84-90, Chapter 21, 181-186. California: Freedom Press, 2003.

Jacob S, Lawrence R, Zucker M, *The Miracle of MSM—The Natural Solution for Pain*. New York: Library of Congress Cataloging-in-Publication Data, 1999.

Jacob SW, Herschler R. *Pharmacology of DMSO*, Cryobiology, 1985, 23(1):14-27.

Jacob, S.W. and Wood, D.C. *Dimethyl sulfoxide (DMSO): Toxicology, pharmacology, and clinical experience*. Am. J. Surg. 1967; 114(3):414-426.

Jagannath C, Reddy VM, Gangadharam PR. *Enhancement of drug susceptibility of multi-drug resistant strains of Mycobacterium tuberculosis by ethambutol and dimethyl sulphoxide*. J Antimicrob Chemother. Mar. 1995; 35(3):381-90.

Jimenez RA, Willkens RF. *Dimethyl Sulphoxide: a perspective of its use in rheumatic diseases*. J Lab Clin Med 1982; 100(4):489-500.

John, H., Laudahn, G. *Clinical Experiences with the Topical Application of DMSO in Orthopedic Diseases: Evaluation of 4,180 Cases*, Annals New York Academy of Sciences, 1967; vol. 141:506-516.

Karlson AG, Ulrich JA, *Stock solutions of rifampin remain stable in dimethylsulfoxide for at least 8 months*, Appl Microbiol. Oct. 1969; 18(4):692-3.

Kim, et al. *Efficacy of Methylsulfonylmethane (MSM) In Osteoarthritis Path of The Knee: A Pilot Clinical Trial*. Osteoarthritis and Cartilage (2006) 14:286-294.

Knowles R. *Clinical Experience with DMSO in Small Animal Practice*, Annals New York Academy Sciences (1967) 141:478-483.

Koenen NJ, Haag RF, BiaP, RoseP. *Perkutane therapie bei aktivierter Gonarthrose*. Munch Med Wochenschr 1996; 138 (31-32):534-538.

Liubinets VI, Kruk MV. *Dimexide in the treatment of endobronchitis in patients with destructive forms of pulmonary tuberculosis*, Zh Ushn Nos Gorl Bolezn. Nov.-Dec. 1969; 29(6):68-71.

Lockie and Norcross. *A Clinical Study on the Effects of Dimethyl Sulfoxide in 103 Patients with Acute and Chronic Musculoskeletal Injuries and Inflammations*, Annals New York Academy Sciences (1967) 141:599-602.

Martin D. and Hauthal H., *Dimethyl Sulfoxide*—Chapter 12. New York: John Wiley & Sons, 1971.

Matsumoto, J. *Clincal Trials of Dimethyl Sulfoxide in Rheumatoid Arthritis Patients in Japan*, Annals New York Academy Sciences. 1967; vol. 141:560-568.

Mitinskaia LA, Iukhimenko NV, Kamaeva VF. *BCG vaccination and increasing the effectiveness of treatment of post-vaccination complications by the use of rifampicin and dimexide*. Probl Tuberk. 1994; (5):4-7.

Mohamaddi F, O'Mara K, Unusual Patient Odor Interfering with Care, Resurrection Medical Center, Chicago, Ill.

Muller U, Urbanczik R. *Influence of dimethyl sulfoxide (DMSO) on restoring sensitivity of mycobacterial strains resistant to chemotherapeutic compounds*, J Antimicrob Chemother. May 1979; 5(3):326-7.

Murav'ev luV, Venikova MS, Peskovskaia GN, Riazantseva TA, Sigldin laA. *Effect of dimethylsulphoxide and dimethyl sulfone*. Patol Fiziol Eksp Ter Mar.-Apr. 1991; (2):37-39.

Nash DR, Steingrube VA. *In vitro drug sensitivity of M. avium-intracellulare complex in the presence and absence of dimethyl sulfoxide*. Microbios. 1982; 35(140):71-8.

Oshima Y, Theodosakis J, Amiel D. *The Effect of Distilled Methylsulfonylmethane (MSM) on Human Chondrocytes in vitro*. World Congress on Osteoarthritis, Ft. Lauderdale, Florida; Osteoarthritis and Cartilage 2007; vol. 15 Supplemental C123:213.

Ostojic et. al. *Laboratory Testing of Cabin Air Filters for The Removal of Reduced-Sulfur Odors*. New Engine Design and Automotive Filtration SAE Special Publications 1998; 1362:41-58.

Paul M. *Interval Therapy with Dimethyl Sulfoxide*. Ann NY Acad Sci Mar. 1967; 1(141):586-598.

Paulus E. *FDA advisory committee meeting: methotrexate; guidelines for the clinical evaluation of anti-inflammatory drugs; DMSO in scleroderma*. Arthritis & Rehumatism Oct. 1986; 10(29):1289-1290.

Penrod, D., Bacharach, B., Templeton, J. *Dimethyl Sulfoxide for Incisional Path after Thoracotomy: Preliminary Report*. Annals New York Academy Sciences Mar. 15, 1967; vol. 141(1):493-495.

Potzz GE, Rampey JH, Bejamin F. *The effect of dimethyl sulfoxide (DMSO) on antibiotic sensitivity of a group of medically important microorganisms: preliminary report*. Ann NY Acad Sci. Mar. 15, 1967; 141(1):261-72.

Ropek M, Pawlowska I, Szydlowska T. *Effects of dimethyl sulfoxide on tubercle bacilli resistant to INH*. Gruzlica. Aug. 1971; 39(8):738-41.

Seibert F, Farrelly F, Shepherd C. *DMSO and other combatants against bacteria isolated from leukemia and cancer patients*. Ann NY Acad Sci Mar. 1967; 1(141):175-201.

Simon L, et. al. *Efficacy and Safety of Topical Diclofenac containing Dimethyl Sulfoxide (DMSO) compared with those of Topical Placebo, DMSO Vehicle and Oral Diclofenac for Knee Osteoarthritis*. Pain, 143(2009):238-245.

Smith G, Bertone AL, Kaeding C, et al. *Anti-Inflammatory effects of topically applied dimethyl sulphoxide gel on endotoxin-induced synovitis in horses*. Am J Vet Res Sep. 1998; 59(9):1149-52.

Steinberg, A. *The employment of DMSO as an anti-inflammatory agent and steroid transporter in diversified clinical diseases*. Ann NY Acad Sci 1967, 141(1):532-550.

Szydlowska T. *In Vitro and In Vivo Studies on the role of Dimethylsulfoxide (DMSO) in Resensibilization of Bacterial Strains Resistant to Antibiotics and Chemotherapeutic Agents*. Zbl. Bakt. Hyg., I. Abt. Orig. A 239, 270-274 (1977).

Szydlowska T, Pawlowska I. *Comparative Studies on the Influence of Dimethylsulfoxide (DMSO) on Reversion to Sensitivity to Isonicotinic Acid Hydrazide (INH) and Rifampicin (RMP) in Resistant Strains of Tubercle Bacilli*. Arch Immunol Ther Exp (Warsz). 1976; 24(4):575-77.

Szydlowska T, Pawlowska I. *In vivo studies on reversion to sensitivity of INH-resistant tubercle bacilli under the influence of dimethylsulfoxide (DMSO)*. Arch Immunol Ther Exp (Warsz). 1974; 22(4):559-61.

Szydlowska T. *Studies on the role of dimethylsulfoxide in resensibilization of antibiotic-resistant bacterial strains*. Arch Immunol Ther Exp (Warsz). 1972; 20(2):193-202.

Szydlowska T. *Studies on the role of dimethylsulfoxide in resensibilization of bacterial strains resistant to sulfonamides*. Arch Immunol Ther Exp (Warsz). 1972; 20(2):203-207.

Teigland MB, Saurino V. *Clinical Evaluation of Dimethyl Sulfoxide in Equine Applications*. Ann NY Acad Sci Mar. 1967; 141(1):471-7.

Usha PR, Naidu MUR. *Randomized, double-blind, parallel, placebo-controlled study of oral glucosamine, methylsulfonylmethane and their combination in osteoarthritis*. Clin Drug Invest 2004; 24(6):353-63.

Vuopala U, et. al. *The Analgesic action of DMSO ointment in arthrosis*. Acta Rheum Scand 1971; 17(1):57-60.

Wood, DC, Wood, J. *Pharmacologic and Biochemical Considerations of Dimethyl Sulfoxide*. Ann NY Acad Sci Jan. 1975; 243:7-19.

Zuckner, J. Uddin, J., Gantner, G. *Local Application of Dimethyl Sulfoxide and DMSO Combined with Triamcinolone Acetonide in Rheumatoid Arthritis*. Ann NY Acad. Sci. Mar. 1967; 1(141):555-9.

Wierzbicki; Homocysteine and cardiovascular disease: a review of the evidence; Diabetes and Vascular Disease Research; Jun. 2007; pp. 143-149; vol. 4, Iss 2; The British Library.

Jacob et al., Interstitial Cystitis Network—Chat Log, Topic: Understanding DMSO; Mar. 28, 2000; The IC Network.

Baer P, Thomas L, Shainhouse JZ. Treatment of osteoarthritis of the knee with a topical diclofenac solution: a randomized, controlled 6-week trial. BMC Musculoskeletal Disord. 2005; 6:44.

Pennsaid Monograph, Nuvo Research, 2010.

Rosenbaum WM, Rosenbaum EE, Jacob S. The use of dimethyl sulfoxide (DMSO) for the treatment of intractable pain in surgical patients. Surgery 1965: 58.

Roth SH, Shainouse JZ, Efficacy of Safety of a topical diclofenac solution (Pennsaid) in the treatment of primary osteoarthritis of the knee: a randomized, double-blind, controlled clinical trial. Arch Intern Med. Oct. 11, 2004;164(18):2017-23.

Shainhouse JZ, Grierson L, Naseer Z, A long-term, open-label study to confirm the safety of topical diclofenac solution containing dimethyl sulfoxide in the treatment of the osteoarthritic knee, American Journal of Therapeutics 0(0) 2010.

Tugwell PS, Wells GA, Shainhouse JZ. Equivalence study of a topical diclofenac solution (Pennsaid) compared with oral diclofenac in symptomatic treatment of osteoarthritis of the knee: a randomized, controlled trial. J Rheumatol. Oct. 2004; 31(10):1893-5.

Cherian L, Robertson C. *L-Arginine and Free Radical Scavengers Increase Cerebral Blood Flow and Brain Tissue Nitric Oxide Concentrations after Controlled Cortical Impact Injury in Rats*. Journal of Neurotrauma, vol. 20, No. 1, 2003; (Jan. 2003), pp. 77-85.

Kubota et al. *Beneficial effect of L-Arginine for Stroke-like episode in MELAS* Brain and Development, Amsterdam, JL, vol. 26, No. 7, Oct. 1, 2004; pp. 481-483.

Robertson et al. "*L-Arginine reduces neuronal damage after traumatic brain injury in the mouse*" Journal of Neurotrauma, vol. 17, No. 10, Oct. 2000, p. 945.

Shaklee Health Network, "Methyl Sulfonyl Methane," [online], 2006 [retrieved on Dec. 16, 2010]. Retrieved from the internet: <URL:http://content.hbiondemand.com/shap/monoVMN.asp?objID=100028]: p. 1-4, especially p. 1, para 1 to p. 2, para 1.

Additive Free MSM Methylsulfonylmethane. World Image Naturals™, Inc. 2005. Downloaded from http://www.worldimagenaturals.com/products/msm/index.php. pp. 1-6.

AloeCalm™ All-Natural and Organic Body Lotion. Lanique Botanicals™. Downloaded from http://www.acne-answers.org/products/aloe-calm.html on Jul. 5, 2010. pp. 1-5.

Andrews, Jennifer M.: "Determination of minimum inhibitory concentrations," Journal of Antimicrobial Chemotherapy (2001) 48, Suppl. S1, 5-16.

Barrager, et al. A Multicentered, Open-Label Trial on the Safety and Efficacy of Methylsulfonylmethane in the Treatment of Seasonal Allergic Rhinitis, The Journal of Alternative and Complementary Medicine, vol. 8, No. 2, 2002, pp. 167-173.

Beilke, et al.: "Effects of dimethyl sulfoxide on the oxidative function of human neutrophils," (1987) Journal of Laboratory and Clinical Medicine 110:91-96.

Borodina, et al.: "Dimethylsulfone as a growth substrate for novel methylotrophic species of *Hyphomicrobium* and *Arthrobacter*," Arch Microbiol (2000) 173: 425-437.

Brandt, et al.: "Selective Affinity of Dimethyl Sulphoxide (DMSO) and 2-amino-4- phenylsulphonylbenzenesulphonamide (NSD 3004) for the Large Intestinal Mucosa of Mice," Acta pharmacol. Et toxicol. 1982, 51, 173-176.

Brown, Derek, F.J., et al.: "Guidelines for the laboratory diagnosis and susceptibility testing of methicillin-resistant *Staphylococcus aureus* (MRSA)," Journal of Antimicrobial Chemotherapy (2005) 56, 1000-1018.

Dancer, S. J.: "The effect of antibiotics on methicillin-resistant *Staphylococcus aureus*," Journal of Antimicrobial Chemotherapy (2008) 61, 246-253.

de Lencastre, et al.: "Antibiotic resistant *Staphylococcus aureus*: a paradigm of adaptive power," Curr Opin Microbiol. Oct. 2007; 10(5): 428-435.

Gerhards & Gibian, "The Metabolism of Dimethyl Sulfoxide and Its Metabolic Effect in Man and Animals," Annals New York Academy of Sciences, pp. 65-76, Mar. 1967.

Gupta, Shyam Dr.: "New Delivery System for Topical Nutraceutical (Nutracosmetic) and Cosmeceutical Formulations," pp. 1-5, Business Briefing: Global Cosmetics Manufacturing 2004.

Horváth, et al.: "Toxicity of methylsulfonylmethane in rats," Food and Chemical Toxicology 40 (2002) 1459-1462.

How to Flush the Toxins out of Your Body from the Swine or H1N1 Flu Shot, downloaded from http://www.ehow.com/print/how_5625054_flush-swine-hn-flu-shot.html, on Aug. 18, 2010. pp. 1-3.

Hucker, et al.: "Studies on The Absorption, Excretion and Metabolism of Dimethylsulfoxide (DMSO) in Man," The Journal of Pharmacology and Experimental Therapeutics, 155:309-317. 1967.

Jacob & Herschler: "Introductory Remarks: Dimethyl Sulfoxide After Twenty Years," Annals New York Academy of Sciences, Jun. 1983.

Kocsis, et al., "Biological Effects of The Metabolites of Dimethyl Sulfoxide", Ann N.Y. Acad. Sci. 243, 104 09 (1975).

Layman, et al.: "The Absorption, Metabolism and Excretion of Dimethyl Sulfoxide by Rhesus Monkeys," Life Sciences, vol. 37, pp. 2431-2437, 1985.

Lee, et al.: "Evaluation of Genotoxicity on Plant-Derived Dietary Sulfar," J. Microbiol. Biotechnol. (2006), 16(5), 817-820.
Lu, et al.: "A Mouse Model for the Evaluation of Pathogenesis and Immunity to Influenza A (H5N1) Viruses Isolated from Humans," Journal of Virology, Jul. 1999, p. 5903-5911.
Magnuson, et al.: "Oral developmental toxicity study of methylsulfonylmethane in rats," Food and Chemical Toxicology 45 (2007) 977-984.
Magnuson, et al.: "Pharmacokinetics and Distribution of [$^{35}$S]Methylsulfonylmethane following Oral Administration to Rats," J. Agric. Food Chem. 2007, 55, 1033-1038.
Methylsulfonylmethane—Wikipedia, the free encyclopedia. Download from http://en.wikipedia.org/wiki/Methylsulfonylmethane, on Jul. 5, 2010. pp. 1-5.
MSM—MethylsulfonylMethane. Downloaded from http://pages.prodigy.net/naturedoctor/msm.html on Jul. 5, 2010. pp. 1-6.
Pratt, et al.: "A Study of the Absorption of OptiMSM (Methylsulfonylmethane) in Horses," Proceedings of the 17th Equine Nutrition and Physiology Society, 2001.
Shanmugam, et al.: "The Effect of Methylsulfonylmethane on Hair Growth Promotion of Magnesium Ascorbyl Phosphate for the Treatment of Alopecia," Biomolecules & Therapeutics, 17(3), 241-248 (2009). ISSN 1976-9148.
Stürenburg, Enno: "Rapid detection of methicillin-resistant *Staphylococcus aureus* directly from clinical samples: methods, effectiveness and cost considerations," GMS German Medical Science 2009, vol. 7, ISSN 1612-3174. pp. 1-19.
Sulfur—MSM—methyl sulfonyl methane—Natural Health Site. A Basic Essential Nutrient Needed Now, More than Ever Before. Downloaded from http://www.all-natural.com/msm.html on Aug. 11, 2010. pp. 1-7.
Szmant, Harry H., "Physical Properties of Dimethyl Sulfoxide and Its Function in Biological Systems," Annals New York Academy of Sciences, pp. 20-23, Jan. 1975.
Tiews, et al.: "Metabolism and Excretion of Dimethyl Sulfoxide in Cows and Calves After Topical and Parenteral Application," Annals New York Academy of Sciences, pp. 139-150. Jan. 1975.
Vignes, Robert P., Ph.D: "Dimethyl Sulfoxide (DMSO): A Superior Solvent," Semiconductor Safety Association, Annual Meeting Apr. 25-28, 2000, Arlington, VA. pp. 1-47.
Wiesinger, Heinrich "Arginine metabolism and the synthesis of nitric oxide in the nervous system," Progress in Neurobiology 64, 365-91, 2001.
Williams, et al.: "Metabolism of Dimethyl Sulfide, Dimethyl Sulfoxide, and Dimethyl Sulfone in the Rabbit," Archives of Biochemistry and Biophysics 117, 84-87 (1966).
Windrum, et al.: "Variation in dimethyl sulfoxide use in stem cell transplantation: a survey of EBMT centres," Bone Marrow Transplantation (2005) 36, 601-603.
Wong, et al.: "Absorption, Excretion, and Biotransformation of Dimethyl Sulfoxide in Man and Minature Pigs After Topical Applicaton As an 80% Gel," The Journal of Investigative Dermatology, vol. 56, No. 1, 1971.
Zhang, et al.: "Assessment of methysulfonylmethane as a permeability enhancer for regional EDTA chelation therapy," infoma healthcare, Drug Delivery, 2009, 16(5): 243-248.

* cited by examiner

MATERIALS FOR FACILITATING ADMINISTRATION OF DIMETHYL SULFOXIDE (DMSO) AND RELATED COMPOUNDS

RELATED APPLICATIONS

This application is the U.S. National Phase under 35 U.S.C. §371 of International Application No. PCT/US2006/035499, filed Sep. 11, 2006 (published as WO 2007/033180A1), which claims priority to United States Provisional Application Ser. Nos. 60/716,265 and 60/716,368, both of which were filed Sep. 12, 2005, and all applications are herein incorporated by reference.

BACKGROUND OF THE INVENTION

1. Field of the Invention

The invention relates generally to materials for facilitating the administration of dimethyl sulfoxide (DMSO) and related compounds. In one embodiment, the invention comprises a kit comprising some or all of the items desired for the safe and effective administration of DMSO to medical patients in a hospital, ambulance, EMT or other environment. In another embodiment, the invention relates to polymeric materials used to construct devices, such as indicating containers, that facilitate DMSO administration.

2. Description of the Related Art

With the greatly increased use and anticipated use of DMSO in medical treatments for serious injuries and illness, technology that facilitates the administration of DMSO is becoming increasingly important. Although DMSO has several uses as a medicament, many clinicians are reluctant to administer DMSO to their patients because of the difficulty in administering DMSO. Not only does the metabolism of DMSO produce noxious odors, but DMSO is a member of the subset of chemical compounds known as "super solvents" because few polymers are insoluble in DMSO. Because most compounds dissolve in DMSO, containers for holding or delivering DMSO in a manner that does not cause leaching of (or chemical reactions with) DMSO are not readily available.

The IV tubing most commonly used today in hospitals is plasticized PVC (polyvinyl chloride) wherein both the PVC and the plasticizers are readily dissolved by DMSO. Substitutes for PVC and its plasticizers that have been incorporated in the recent art also are a cancer and other serious health risk and will dissolve in DMSO. Examples of DMSO soluble chemicals include PVC and its plasticizers DEHP and TOTM, acrylics, styrenes, polyamides, urethanes and silicones. The danger of DMSO in use with common polymers poses serious risk. Not only will common polymers be degraded by DMSO such that perforations will cause ineffective containment of DMSO, but the degradation or reaction with DMSO of certain polymers can result in toxic by-products.

Polyolefins such as polybutylene, polypropylene, polyethylene, and their copolymers are insoluble in DMSO, but tubing formed from these materials is known to kink and crack too easily for use in IV systems. Similarly, bags made of these materials are difficult to form and may not withstand severe handling. An additional complication is the known fact that few polymers bond to polyolefins.

Likewise, although medical kits and IV kits are routinely used in ambulatory and hospital settings, Applicant believes that no such kits are available that address the specific safety and handling requirements of DMSO. As DMSO becomes a much more routine drug of choice for the treatment of seriously ill or injured patients, the success of these treatment methods will require immediate access to all of the particular items necessitated by the presence of DMSO and related compounds. Patient treatment items must be immediately available in sterile condition. These items are simply hot currently available in ordinary hospital, ambulance, EMT or medical practice.

SUMMARY OF THE INVENTION

Preferred embodiments of the invention relate to materials to facilitate the administration of DMSO and associated compounds.

Several embodiments of the present invention relate to a material designed to withstand exposure to DMSO and associated compounds. In one embodiment, the invention comprise a container for holding or transporting DMSO and/or associated compounds. The term "container" as used herein shall be given its ordinary meaning and shall include carriers, holders, enclosures, and conduits for containing, holding, administering, delivering, or transporting materials such as DMSO and associated compounds.

The phrases "DMSO associated compounds", "associated compounds", or related compounds as used herein shall be given their ordinary meaning and shall include degradation compounds, derivatives, precursors, and metabolites of DMSO, such as methylsulfonylmethane (MSM or $DMSO_2$) and dimetlhyl sulfide or methylthiomethane (DMS).

The phrase "DMSO container" as used herein shall be given its ordinary meaning and shall include containers that are adapted to contain DMSO and associated compounds.

The term "kit" as used herein shall be given its ordinary meaning and shall also mean a system, grouping, and collection of materials provided for a common goal.

In one embodiment, the invention comprises a device for facilitating administration of DMSO. The device comprises a container for holding or delivering DMSO wherein the container comprises an inner layer, an outer layer, and an intermediate layer. The inner layer comprises a material that is insoluble in DMSO. The inner layer may also be impervious to fluids. The intermediate layer comprises a material that contacts the inner layer and outer layer. The outer layer is resistant to abrasion. The container may be an IV bag, tubing, a syringe, or a catheter.

In one embodiment of the invention, the DMSO container comprises a single or multilayer material for safely and effectively containing DMSO. In one embodiment, the material is polymeric.

In one embodiment, the inner layer of the container comprises a material that will not dissolve in DMSO or related compounds. Thus, in some embodiments, the inner layer will be able to endure exposure to DMSO (for minutes, hours, days, months, or longer) without changing the chemical or physical nature of the container. In one embodiment, the inner layer of the container is insoluble, inert, and/or non-reactive with DMSO. The inner layer may comprise a homophase copolymer of propylene.

In one embodiment, the outer layer comprises a thermoplastic polymer, and is resistant to abrasion.

In one embodiment, the intermediate layer comprises a binding layer for binding the inner layer and said outer layer. The intermediate layer may comprises a polyamide film that bonds said inner layer and said outer layer. The intermediate layer may comprise a 9 through 13-aminoundecanoic acid polyamide. The intermediate layer may comprise a polyolefin.

In another embodiment, the invention comprises a DMSO container and an indicator to indicate that DMSO has leached through one or more layers of the container. The indicator may be on the inside or outside of the container. The indicator may be integral with the container, coupled to the container, or a separate component. The indicator may be located on or within the inner layer. The indicator may be located on the outside of the inner layer, or in between the inner layer and the intermediate layer. The indicator may be located in between the intermediate layer and the outer layer.

In one embodiment, the indicator comprises a visual indicator or colorant that changes color if DMSO leaches out of the inner layer. The colorant may warn of commingling of the layers during manufacturing, a manufacturing failure that could result in the intermediate layer being exposed to DMSO and leaching into the IV solution. In one embodiment, at least one portion of the container is transparent so as to visually indicate a color change. The indicator may comprise a compound, such as a chemical compound, that reacts or changes color upon exposure to DMSO, and is thereby adapted to signal escape of DMSO from the inner layer (or another layer) of said container. The indicator may comprises a compound that changes light transmission upon exposure to DMSO, and is thereby adapted to signal escape of DMSO from the inner layer of said container.

In a further embodiment, the invention comprises making a container according to any one of the embodiments described herein. In one embodiment, the material for the container is made by co-extrusion.

Several embodiments of the present invention relate to a medical supply kit assembled for the purpose of making the necessary items available to medical personnel administering DMSO and related compounds to medical patients in hospital, ambulance, or EMT conditions. In one embodiment, the invention comprises all of the specific items required for the administration of DMSO. Several embodiments of the invention comprise kits to make the administration of DMSO and its associated compounds as efficient, effective and safe as possible.

In one embodiment, the invention comprises a kit comprising one or more of the containers according to any one of the embodiments described herein. In one embodiment, the kit further comprises one or more of the following: instructions for use; a DMSO resistant stainless steel IV needle; a DMSO resistant IV catheter; a syringe; and DMSO. The kit may also contain other components, as described below.

In one embodiment, the kit comprises a detector for detecting the presence of DMSO or related compound. The kit may also include adsorbant material for adsorbing the noxious odors associated with DMSO metabolism. The adsorbant material, includes, but is not limited to, caps, gowns, scrubs, and linens.

In another embodiment, the kit comprises at least one adsorbent depletion indicating cartridge for a respiratory ventilator exhaust to capture the metabolites of DMSO passing from the respiration of the patient.

In yet another embodiment, the kit comprises at least one pair of protective caregiver gloves constructed of a suitable hypoallergenic rubberized material including modified or unmodified structures of singular polyolefins and/or combinations of polyolefins or the extruded multilayer film as for the IV bag or IV tubing.

In one embodiment, the invention comprises a method for facilitating the administration of dimethyl sulfoxide (DMSO) or related compounds to a recipient. In one embodiment, the method comprises providing a device or container according to any one of the embodiments described herein. The method may also include providing dimethyl sulfoxide (DMSO) or a related compound. Additionally, a kit or kit components may be provided, along with instructions for use.

DETAILED DESCRIPTION OF THE PREFERRED EMBODIMENT

Embodiments of the present invention will be described as it applies to certain preferred embodiments. It is not intended that the present invention be limited to the described embodiment. It is intended that the invention cover all modifications and alternatives which may be included within the spirit and scope of the invention.

Preferred embodiments of the present invention comprise materials and devices to facilitate handling or administration of DMSO and associated compounds, and methods of making and using same.

In one embodiment, the invention comprises IV bags, tubing, and other carriers, containers, and conduits for DMSO and associated compounds.

In another embodiment, the invention comprises kits for the delivery and administration of DMSO and associated compounds.

Carriers, Containers, And Conduits For DMSO And Associated Compounds

In one embodiment, the invention comprises a container (including carriers and conduits such as IV bags and tubing) for holding or transporting DMSO and/or associated compounds. In one embodiment, the DMSO container comprises a plurality of layers.

In one embodiment, the DMSO container comprises three layers: at least one inner, fluid resistant, layer; at least one binding layer; and at least one outer, protective, layer.

In one embodiment, the first layer comprises a DMSO resistant homophase copolymer of propylene, wherein the polypropylene is a known material and is appreciated in many fields. In one embodiment, the first layer is capable of withstanding concentrations of DMSO of a trace to as much as 100% at temperatures up to the melting point in the range of about 110 to 160 degrees C. In one embodiment, heterophase polymers that are DMSO resistant may be used.

In one embodiment, the first layer comprises a homophase copolymer of propylene that contains from about 1% to 50% by weight of polyethylene and can be employed to particular advantage in the bonding of the layers.

In one embodiment, the intermediate binding layer may comprises suitable polyolefin binders. In another embodiment, the intermediate layer comprises at least one binding polymer. The binding polymer includes, but is not limited to, 13-aminoundecanoic acid, 12-aminoundecanoic acid, 11-aminoundecanoic acid, 10-aminoundecanoic acid, and 9-aminoundecanoic acid polyamide films. In one embodiment, the intermediate binding layer may comprise a transparent visual indicator or other indicator, or a combination of two or more indicators. The indicator that may be coupled to the intermediate layer may be in addition to, in instead of, the indicator that is coupled to the inner layer.

In one embodiment, the outer, protective, layer of the container (such as tubing and bags) comprises a polymer. In one embodiment, the outer layer comprises a tough, abuse-resistant thermoplastic polymers including, but not limited to, polyvinylidene chloride (PVDC) or ethylene vinyl alcohol (EVOH), or other polyamides.

In one embodiment, the outer layer is resistant to abrasion. Sealants may be used instead of or in addition to the outer layer. An indicator may be part of, coupled to, or integral with the outer layer.

In one embodiment, the container comprises one or more indicators. The indicator will indicate or signal the escape of DMSO or associated compounds from the inner layer. In one embodiment, a visually indicating transparent colorant is included as an integral part of the homophase copolymer of the inner layer. Such transparent visual indicator (or other type of indicator) warns of commingling of the inner and intermediate layers during manufacture subjecting the DMSO soluble intermediate layer to the possibility of leaching into the IV solution. This becomes a significant quality control point for the products manufactured utilizing this method. This transparent color indicator also provides immediate identification by the caregiver of materials suitable for use with DMSO. An example of potential indictors would be a gold fleck completely immune to interaction with DMSO and associated compounds. Other indicators may be used as well. One advantage of an indicator according to some embodiments is that the indicator will promptly signal when DMSO or an associated compound has escaped from a safe layer (a layer that will not dissolve in DMSO) to a layer that is reactive or soluble with DMSO.

In one embodiment, the indicator comprises a light transmission changing indicator, such as a coating. In one embodiment, a plurality of microparticles may be dispersed between the layers of the container. A reagent formulated to change color and/or light transmission in response to the presence of moisture and/or DMSO in said matrix may be provided to indicate that DMSO and/or an associated compound has escaped the inner layer.

Some indicators may be sensitive to the chemical structure of DMSO and/or associated compounds. Some indicators may be sensitive to moisture content, while other indicators may signal the presence of gaseous molecules or frames.

In one embodiment, indicators which change from translucent to clear are provided. Such indicators include, but are not limited to, metal chlorides, metal fluorides, metal hydroxides, metal carbonates, and metal nitrates. In one embodiment, alkali metal chlorides, alkaline earth metal chlorides or transition metal chlorides are used as indicators. These may be selected from the group alkali metal ozonide, lithium chloride, sodium hydroxide, potassium fluoride, potassium carbonate, potassium nitrate, magnesium chloride, stannous chloride, strontium chloride, aluminum chloride, calcium chloride, zinc chloride, calcium nitrate, sodium nitrate, ammonium chloride and ammonium nitrate. In some embodiments, these indicators will turn clear upon contact with moisture. In some embodiments, the presence of DMSO will increase the rate or intensity at which the indicators turn clear.

In one embodiment, a color changing indicating layer is provided. The indicator layer. The indicator layer of the container (which may be an additional layer or integral with the inner, intermediate, or outer layer) may comprise DMSO-absorptive or hygroscopic plastic such as cellulose acetate, cellulose acetate butyrate or a nylon, such as Nylon 408, and optionally, a fluid such as water. A cobalt salt is applied to, coupled with, or integral with the surface of the layer to provide a portion of the container characterized by a specific color in the absence of moisture and color change in the presence of moisture. Examples of cobalt salts which can be used include cobaltous chloride and cobaltous bromide. Various hygroscopic modifiers may also be added to enhance the moisture-grabbing properties of the hygroscopic plastic. Two of these hygroscopic modifiers include zinc chloride and calcium chloride. The quantity of hygroscopic modifiers hygroscopic may be varied to effect the moisture range to which the indicator is sensitive. In one embodiment, the change in color of a cobalt salt when moisture is introduced will be distinctive. For example, the color of cobaltous chloride is normally bluish when in a dry state but the color rapidly changes to a pinkish hue as moisture is absorbed by the hygroscopic plastic base. Likewise, the dry color of cobaltous bromide is greenish and the color changes to a yellowish hue as moisture is introduced. To obtain a desired initial or dry color, the aforementioned salts may be mixed.

In one embodiment, the indicator comprises a light transmission changing layer. The indicator layer of the container (which may be an additional layer or integral with the inner, intermediate, or outer layer) may comprise a DMSO-absolptive plastic such as cellulose acetate, cellulose acetate butyrate or a nylon, such as Nylon 408, and optionally, a fluid such as water. Particularly with the presence of DMSO, these materials would quickly turn from clear to cloudy or from transparent to translucent. Thus, in one embodiment, a cloudy or translucent appearance could be visually observed by a user. Alternatively, a light may be passed through the layer to detect cloudiness or translucency.

In one embodiment, a tubing expressly used to convey an IV solution bearing from a trace to as much as 100% DMSO, but preferentially in the range of 5 to 30% DMSO and/or associated compounds, is provided.

In another embodiment, a weldable bag to be used to store and dispense an IV solution bearing from a trace to as much as 100% DMSO, but preferentially in the range of 5 to 30% DMSO and/or associated compounds is provided.

In yet another embodiment, an easily inspectable device clearly indicating its suitability for use in DMSO bearing IV solutions is provided.

In a further embodiment, delivery of DMSO or DMSO related compounds for the prevention or treatment of illnesses is provided. In a preferred embodiment of the device, treatment of severe head injury, spinal chord injury, stroke or other neuropreventative/neurotherapeutic treatments is provided.

The inner layer, intermediate layer, and outer layer may have a individual or total thickness of about 0.0001 microns to about 10 cm. In one embodiment, each layer is about 0.0003 microns to about 4 cm thick. In one embodiment, the inner layer is about 1 mm to about 1 cm thick, the intermediate layer is about 1 mm to about 1 cm thick, and the outer layer is about 0.1 mm to about 1 cm thick. The thickness of each layer will depend on whether the container is an IV bag, tubing, a catheter, or a syringe. In some embodiments, the container comprises only one layer. In other embodiments, the container comprises more than three layers. In one embodiment, a layer may simply be a coating or dusting of particles.

In some embodiments, the containers will comprises features that are suited for the particular use of that container. Such features may be determined based on testing criteria. Testing criteria may be selected from a variety of testing methods. These may be similar to that described in U.S. Pat. No. 5,998,019, herein incorporated by reference. For example, a container may have specific properties that relate to autoclavability, low temperature ductility, mechanical modulus and recovery, RF processibility, optical clarity, strain whitening, environmental compatibility, and solution compatibility.

In several embodiments, the material selected for the construction of the container is based on the ability of the material to seal or close.

In other embodiments, the material selected for the construction of the container is based on compatibility with DMSO and other fluids, as for example, described in U.S. Pat. No. 5,998,019, herein incorporated by reference.

Kits For The Delivery And Administration of DMSO And Associated Compounds

In several embodiments, the present invention comprises a kit that facilitates the administration of DMSO and associated compounds. In one embodiment, the kit comprises several parts which are selected to be inclusive of all items needed for the procedure and to provide the features, resistance, and/or absorbency required by the special nature of DMSO and associated compounds.

In one embodiment, the kit comprises at least one container that comprises one of the layers described herein. The container included in the kit may be an IV bag, tubing, catheter, syringe, etc.

The list of materials for the DMSO IV kits may include, but is not limited to, the following components and may be divided as shown or in other ways as needed by the medical teams:

1. Patient Treatment Kit (Sterile Items):

In one embodiment, a surgical treatment kit or therapeutic treatment kit for treating patients with DMSO or DMSO compounds is provided. In one embodiment, the kit is specifically resistant to DMSO or DMSO compound and comprises one or more (and preferably, two or more) of the following:

a. Instructions for the procedure which may printed in fonts sized to be seen from across the room on large format E sized drawing paper. Each step is illustrated as well as described in detail. The instructions may be printed on the packaging material.

b. A full set of DMSO resistant Stainless Steel IV needles sized 16, 18, 19, 20, 21, 22 and 23 gauges. Said needles may be encased in moisture resistant packaging and accompanied by a corrosion inhibiting desiccant pad. A partial set or single needle can be included instead of the full set.

c. A full set of DMSO resistant IV Catheters sized to match the needles: 16, 18, 19, 20, 21, 22 and 23 gauges. A partial set or single catheter can be included instead of the full set.

d. Syringes in 10 ml, 20 ml and/or 50 ml sizes for the use of the medical professional should additional medicants be required in the IV.

e. The IV solution including DMSO in concentrations of about 1 volume percent through about 40 volume percent where the preferred concentration is about 28 volume percent. Additional compounds associated with DMSO IVs may be included. Concentrations less than 1% and higher than 40% may be provided in certain embodiments.

f. IV Bag or other container for the purpose of containing the above solution. Such bag may be marked with multiple linear scales including milliliters, DMSO dosage, and patient body weight. Included affixed to subject bag is a septum suitable for receiving additional medicament applied through use of the above syringes. The materials of construction for the subject bag comprise a multilayer film with the solution contacting liner completely resistant to DMSO and related compounds, an intermediate bonding layer and an outer abrasion resistant layer.

g. One or more containers that is manufactured by co-extrusion as a multilayer film with the solution contacting liner completely resistant to DMSO and related compounds, an intermediate bonding layer and an outer abrasion resistant layer.

h. Multiple tubing lengths and connectors and Y connectors to be used for special applications.

i. 'Hoffmann' style tubing clamps sized and uniquely structurally designed to match the durometer and diameter DMSO resistant tubing in the other parts of the kit.

j. Tape with a base paper or fabric and an adhesive selected to be resistant to the metabolites of DMSO and in particular to DMS (dimethyl sulfide) and to avoid all allergic combinations with DMS and associated compounds. Such tape to be used for affixing the tubing and catheter assembly to the patient and for applying a bandage to the needle puncture area.

k. Betadyne or equivalent sponges and alcohol wipes or other hypoallergenic non-DMSO or DMS or DMSO metabolite reacting preparatory fluid for the injection area of the patient.

1. A single use hypoallergenic elastic tourniquet suitable for short term exposure to DMS and the other metabolites of DMSO.

2. Patient Care Kit (Non-Sterile Items)

A kit for providing odor control, chemical monitoring and safety equipment for use in treating patients with DMSO or related compounds (such as DMS) is provided. In a preferred embodiment, the kit comprises one or more of the following:

a. A suitable number of DMSO or related compounds (e.g., DMS) sensitive and indicating patches to pin or clip to the caregiver's clothing for the purpose of detecting and flagging for the caregiver the exposure level to DMS and related compounds.

b. A suitable number of DMSO or related compounds (e.g., DMS) adsorbent surgical style masks for the use of the caregivers to isolate them for the noxious odors of DMS and of the other metabolites of DMSO and associated compounds.

c. The kit may or may not also include protective caregiver caps, gowns, scrubs, and other specially treated adsorbent items to adsorb the noxious patient body odors of DMS and of the other metabolites of DMSO.

d. A DMSO or related compounds (e.g., DMS) and odor adsorbent Patient Quilt to adsorb the noxious patient body odors of DMS and of the other metabolites of DMSO and associated compounds.

e. A DMSO or related compounds (e.g., DMS) or odor adsorbent Patient Gown to adsorb the noxious patient body odors of DMS and of the other metabolites of DMSO and associated compounds.

f. An adsorbent depletion indicating cartridge for a respiratory ventilator exhaust to capture the metabolites of DMSO passing from the respiration of the patient.

g. Protective caregiver gloves constructed of a suitable hypoallergenic rubberized material including modified or unmodified structures of singular polyolefins and/or combinations of polyolefins or the extruded multilayer film as for the IV bag or IV tubing.

h. A suitable number of pairs of safety eyeglasses for the protection of the caregivers from exposure to the IV solution and bodily fluids associated with the procedure.

i. Hypoallergenic pure cotton balls and swabs for use for absorbing IV and bodily fluids associated with the procedure.

j. Additional protective and safety items as needed.

3. Sterile Venous Cut Down Kit

A venous cut down kit may or may not also be included for the purpose of immediately treating a patient where needle entry to the veins is prevented for any reason. Such a sub-kit may include one or more of following:

a. Scalpel b. Hemostats c. Forceps d. Scissors e. Sutures

A Portable Enclosure for the kits is also provided. In one embodiment, the enclosure may be a segmented hard or soft sided case organized in such a way that each item is arranged in the order of use and is readily accessible for selection by the caregiver. Such case is preferentially capable of being opened for display of all items. Individual kit items are clearly marked and identified so as to eliminate as much as possible any question related to the procedure. In one embodiment, the enclosure may comprise a molded or otherwise formed segmented or non-segmented base covered by an easily removable Tyvek® (E. I. Du Pont De Nemours And Company Corporation) or equivalent sheet.

EXAMPLES

The following examples describe non-limiting uses of the materials described herein.

A kit for treating a patient with severe closed head trauma is provided. The time between injury and treatment is extremely short where any success is desired in relieving patient symptoms. In a preferred embodiment, the medical staff would open the kit, fully exposing the contents; display the instructions for all to view and internalize, and proceed stepwise to complete the prescribed medical procedure.

A kit for treating a patient who may have suffered a stroke is provided. While often stroke may be difficult to diagnose, as soon as the diagnoses is clear, the caregivers must proceed immediately with the procedure. In a preferred embodiment, the medical staff would open the kit, fully exposing the contents; display the instructions for all to view and internalize, and proceed stepwise to complete the prescribed medical procedure.

Kits for the neuropreventative or neurotherapeutic treatment of patients diagnosed with, but not limited to, any of the following conditions are provided:

1. Head trauma
2. Stroke
3. Spinal cord
4. Organ Infarction
5. Dimentia
6. Alzheimers
7. CABG
8. Coronary Artery Disease Kits for treatment using DMSO or DMSO related compounds to be applied at or in (but not limited to) one or more of the following environments are provided:

1. Ambulance
2. Hospital
3. Clinic
4. Medical office
5. Home
6. School
7. Sports stadium
8. Work place
9. Police station Kits for treatment using DMSO to be applied in connection with (but not limited to) the following:

1. Neuroprotective
2. Neurotherapeutic

In a preferred embodiment, three kits would be provided for treatment of a patient with DMSO or DMSO related compounds. The first sterile kit, would be housed in a molded or injection formed plastic tray with a Tyvek® (E. I. Du Pont De Nemours And Company Corporation) lid, printed with instructions. The kit would include a 16 and 18 gauge angiocathers with Hoffmann clamps, an IV solution including DMSO in concentrations of 28 volume percent, betadyne or alcohol wipes and elastic tourniquet. The second kit would include non-sterile patient care items of items listed as 2 a, b, d, f, and g. The third kit would be a Venous cut down kit.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A device for facilitating administration of dimethyl sulfoxide (DMSO), comprising:

a container for holding or delivering dimethyl sulfoxide (DMSO), wherein said container comprises an inner layer, an outer layer, an indicator layer, and an intermediate layer;

wherein said inner layer comprises a material that is insoluble in dimethyl sulfoxide (DMSO);

wherein said inner layer comprises a homophase copolymer of propylene containing from about 1% to about 50% of polyethylene;

wherein said indicator layer is disposed between the inner layer and the intermediate layer;

wherein said indicator layer is configured to indicate that dimethyl sulfoxide (DMSO) has escaped from the inner layer, wherein said intermediate layer comprises a binding layer for binding said inner layer and said outer layer; and wherein said outer layer is resistant to abrasion.

2. The device of claim 1, wherein the indicator layer comprises a compound that changes color upon exposure to dimethyl sulfoxide (DMSO), and is thereby adapted to signal escape of dimethyl sulfoxide (DMSO) from the inner layer of said container.

3. The device of claim 1, wherein the indicator layer comprises a compound that changes light transmission upon exposure to dimethyl sulfoxide (DMSO), and is thereby adapted to signal escape of dimethyl sulfoxide (DMSO) from the inner layer of said container.

4. The device of claim 1, wherein the container comprises an IV bag, tubing, a syringe, or a catheter.

5. The device of claim 1, wherein the intermediate layer comprises a polyamide film that bonds said inner layer and said outer layer.

6. The device of claim 1, wherein the intermediate layer comprises a 9 through 13-aminoundecanoic acid polyamide.

7. The device of claim 1, wherein the intermediate layer comprises a polyolefin.

8. The device of claim 1, wherein the outer layer comprises a thermoplastic polymer.

9. A device of claim 1, wherein said device is prepared by co-extrusion.

10. A kit comprising:

a. Instructions for use;

b. At least one dimethyl sulfoxide (DMSO) resistant Stainless Steel IV needle;

c. At least one dimethyl sulfoxide (DMSO) resistant IV Catheter;

d. At least one dimethyl sulfoxide (DMSO) resistant syringe;

e. DMSO; and f. the device of claim 1.

11. The kit of claim 10, wherein said kit further comprises adsorbant material for adsorbing the noxious odors associated with dimethyl sulfoxide (DMSO) metabolism.

12. The kit of claim 11, wherein said adsorbant material is selected from the group consisting of one or more of the following: caps, gowns, scrubs, and linens.

13. A method for facilitating the administration of dimethyl sulfoxide (DMSO) or related compounds to a recipient, comprising:

providing a device according to claim 1; and providing dimethyl sulfoxide (DMSO) or a related compound.

* * * * *